United States Patent
Hu et al.

(10) Patent No.: US 9,271,652 B2
(45) Date of Patent: Mar. 1, 2016

(54) MR SEGMENTATION USING NUCLEAR EMISSION DATA IN HYBRID NUCLEAR IMAGING/MR

(75) Inventors: Zhiqiang Hu, Twinsburg, OH (US); Navdeep Ojha, Mayfield Village, OH (US); Chi-Hua Tung, Aurora, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 235 days.

(21) Appl. No.: 14/001,690

(22) PCT Filed: Mar. 2, 2012

(86) PCT No.: PCT/IB2012/050998
§ 371 (c)(1),
(2), (4) Date: Aug. 27, 2013

(87) PCT Pub. No.: WO2012/120422
PCT Pub. Date: Sep. 13, 2012

(65) Prior Publication Data
US 2013/0336564 A1 Dec. 19, 2013

Related U.S. Application Data

(60) Provisional application No. 61/449,810, filed on Mar. 7, 2011.

(51) Int. Cl.
*G06K 9/00* (2006.01)
*A61B 5/00* (2006.01)
(Continued)

(52) U.S. Cl.
CPC ............ *A61B 5/0033* (2013.01); *G01R 33/481* (2013.01); *G01T 1/1603* (2013.01); *G01R 33/5608* (2013.01)

(58) Field of Classification Search
CPC ............ G01R 33/481; G01R 33/5608; A61B 5/0033; G01T 1/1603
See application file for complete search history.

(56) References Cited

U.S. PATENT DOCUMENTS 6,927,406 B2 * 8/2005 Zyromski .................. 250/496.1
7,002,345 B2 * 2/2006 Jara ......................... G01R 33/50
324/307

(Continued)

FOREIGN PATENT DOCUMENTS

| WO | 2010018478 A1 | 2/2010 |
| WO | 2010032167 A2 | 3/2010 |
| WO | 2010094655 A1 | 8/2010 |

OTHER PUBLICATIONS

Zaidi, H., et al.; Advances in Attenuation Correction Techniques in PET; 2007; PET Clinics; 2(2)191-217.

*Primary Examiner* — Gregory M Desire

(57) ABSTRACT

When generating a magnetic resonance (MR) attenuation map (39), an MR image is segmented to identify a patient's body outline, soft tissue structures, and ambiguous structures comprising bone and/or air. To distinguish between bone and air in the ambiguous structures, a nuclear emission image (e.g., PET) of the same patient or region of interest is segmented. The segmented functional image data is correlated to the segmented MR image data to distinguish between bone and air in the ambiguous structures. Appropriate radiation attenuation values are assigned respectively to identify air voxels and bone voxels in the segmented MR image, and an MR attenuation map is generated from the enhanced segmented MR image, in which ambiguity between air and bone has been resolved. The MR attenuation map is used to generate an attenuation-corrected nuclear image, which is displayed to a user.

22 Claims, 3 Drawing Sheets

(51) Int. Cl.
*G01R 33/48* (2006.01)
*G01T 1/16* (2006.01)
*G01R 33/56* (2006.01)

(56) References Cited

U.S. PATENT DOCUMENTS

| | | | |
|---|---|---|---|
| 8,218,848 B2* | 7/2012 | Lenglet | G06K 9/342 382/131 |
| 2005/0041842 A1* | 2/2005 | Frakes et al. | 382/128 |
| 2005/0281447 A1* | 12/2005 | Moreau-Gobard et al. | 382/130 |
| 2007/0238957 A1* | 10/2007 | Yared | A61B 5/0059 600/407 |
| 2008/0021502 A1* | 1/2008 | Imielinska et al. | 607/1 |
| 2008/0118118 A1* | 5/2008 | Berger | 382/128 |
| 2008/0159610 A1* | 7/2008 | Haas et al. | 382/131 |
| 2008/0273777 A1* | 11/2008 | Luboz | G06T 7/0081 382/130 |
| 2009/0315561 A1* | 12/2009 | Assmann | G01R 33/56375 324/309 |
| 2010/0021034 A1 | 1/2010 | Lenglet et al. | |
| 2010/0204563 A1* | 8/2010 | Stodilka et al. | 600/411 |
| 2010/0261993 A1 | 10/2010 | van der Kouwe et al. | |
| 2013/0336564 A1* | 12/2013 | Hu et al. | 382/131 |

* cited by examiner

MR SEGMENTATION USING NUCLEAR EMISSION DATA IN HYBRID NUCLEAR IMAGING/MR

CROSS REFERENCE TO RELATED APPLICATIONS

This application is a national filing of PCT application Ser. No. PCT/B2012/050998, filed Mar. 2, 2012, published as WO 2012/120422 A1 on Sep. 13, 2012, which claims the benefit of U.S. provisional application Ser. No. 61/449,810 filed Mar. 7, 2011, which is incorporated herein by reference.

The present application finds particular application in combined PET/MR medical imaging systems. However, it will be appreciated that the described technique may also find application in other diagnostic systems, other imaging scenarios, or other diagnostic techniques.

In nuclear imaging, some of the gamma radiation traversing the subject interacts with and is absorbed by the patient's body. Bones and dense tissue absorbs more gamma radiation that soft tissue, which absorbs more gamma radiation than air (e.g., in the lungs). If uncorrected for, these different amounts of radiation attenuation can cause false increase or decrease in relative radioactivity concentration observed in the resultant images. Correction for this attenuation is typically based on an attenuation map, i.e., a map or image of the subject in which each voxel value represents the relative or absolute radiation attenuation properties of the corresponding tissue in the patient.

Nuclear scanners such as positron emission tomography (PET) scanners or single photon emission computed tomography (SPECT) scanners on the current market are sometimes combined with a computed tomography (CT) scanner. In a CT image, the voxel values are indicative of the radiation attenuation properties of the corresponding tissue in the patient. Hence, CT scanners are sometimes used for generating the attenuation map for a nuclear scanner.

Recently, combined nuclear/magnetic resonance (MR) imaging has been proposed. MR scanners image resonating dipoles, particularly the $^1$H dipole of water and lipids. There is no direct correlation between the voxel values of an MR image and the radiation attenuation properties of the corresponding tissue in the patient. An MR image can be used to provide an attenuation map by identifying tissue associated with MR voxels and radiation attenuation properties of the identified tissue. But, there are ambiguities in the mapping, which can lead to a suboptimal attenuation map. For instance, a routine MR image shows cortical bone as dark voxels, but also shows air as dark voxels, which causes a problem in distinguishing cortical bone from air based on image intensity alone. Cortical bone has high radiation attenuation properties and air has very low radiation attenuation properties. Resolving this air/bone ambiguity incorrectly can lead to potentially significant errors in the attenuation map and final PET or SPECT images.

The present application relates to new and improved systems and methods that facilitate distinguishing cortical bone from other tissue or object(s) as represented in an MR attenuation map, which overcome the above-referenced problems and others.

In accordance with one aspect, a system that facilitates resolving ambiguity in a magnetic resonance (MR) image or attenuation map includes an MR reconstruction processor that generates an MR image from raw MR data acquired during a scan of a subject by an MR scanner, and a functional image reconstruction processor that generates a functional image from functional image data acquired during a scan of a subject by a functional image scanner. The system further includes a processor programmed to segment the MR image to generate a segmented MR image having a region of air/bone ambiguity in which ambiguity between air voxels and bone voxels is unresolved, segment the functional image to generate a segmented functional image having bone regions and other regions, and compare the bone regions in the segmented functional image to the bone/air ambiguity region in the segmented MR image to resolve ambiguity between voxels in the bone/air region in the segmented MR image, which correspond to bone and air. The processor is further programmed to assign radiation attenuation values consistent with bone to identified bone voxels, and consistent with air to identified air voxels, in the segmented MR image; and generate an MR attenuation map using the assigned radiation attenuation values.

In accordance with another aspect, a method of resolving ambiguity in an MR image or attenuation map includes generating an MR image from raw MR data acquired during a scan of a subject by an MR scanner, generating a functional image from functional image data acquired during a scan of a subject by a functional image scanner, and segmenting the MR image to generate a segmented MR image having a region of air/bone ambiguity in which ambiguity between air voxels and bone voxels is unresolved. The method further includes segmenting the functional image to generate a segmented functional image having bone regions, comparing at least one of the bone regions and the air regions in the segmented functional image to the bone/air ambiguity region in the segmented MR image to resolve ambiguity between voxels in the bone/air region in the segmented MR image, which correspond to bone and air, and assigning radiation attenuation values consistent with bone to identified bone voxels, and consistent with air to identified air voxels, in the segmented MR image. Additionally, the method includes generating an MR attenuation map using the assigned radiation attenuation values, reconstructing the functional image data into an image using the MR attenuation map to correct attenuation in the functional image data, and displaying the image on a display to a user.

In accordance with another aspect, a method of enhancing an MR attenuation map using nuclear emission data includes segmenting an MR image to identify soft tissue structures and ambiguous structures in the MR image, the ambiguous structures including one or more of bone and air, segmenting a nuclear image to identify bone structures in the nuclear image, and overlaying the segmented nuclear image on the segmented MR image. The method further includes identifying the ambiguous structures in the segmented MR image as either bone or air by comparing the ambiguous structures to the bone structures in the overlaid segmented nuclear image, assigning a first radiation attenuation value to bone voxels identified in the segmented MR image and a second radiation attenuation value to air voxels in the segmented MR image, and generating an MR attenuation map from the segmented MR image.

One advantage is that attenuation map reliability is improved.

Another advantage resides in resolving ambiguity between bone tissue and air pockets in the subject.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

The subject innovation overcomes the aforementioned problems by using nuclear emission data for segmenting bone structures and combining segmented nuclear emission data with an MR image segmentation to derive an accurate attenuation map. An MR-based image of the anatomy is first produced from which outlines of the body, lungs, and various soft tissues can be identified. Although knowledge of physiology can be used to distinguish the lungs and the skeleton, distinguishing air pockets and bone structures, particularly air pockets in bone structures, is ambiguous. In the present application, a nuclear emission image is reconstructed and segmented to identify bone structures, which are compared with ambiguous air-bone structures in the segmented MR image to remove the ambiguity associated with distinguishing air and bone. The innovation may be employed in conjunction with single or multi-tracer nuclear imaging protocols, in which an attenuation map is derived from an anatomic imaging modality such as MR.

Figure 1:
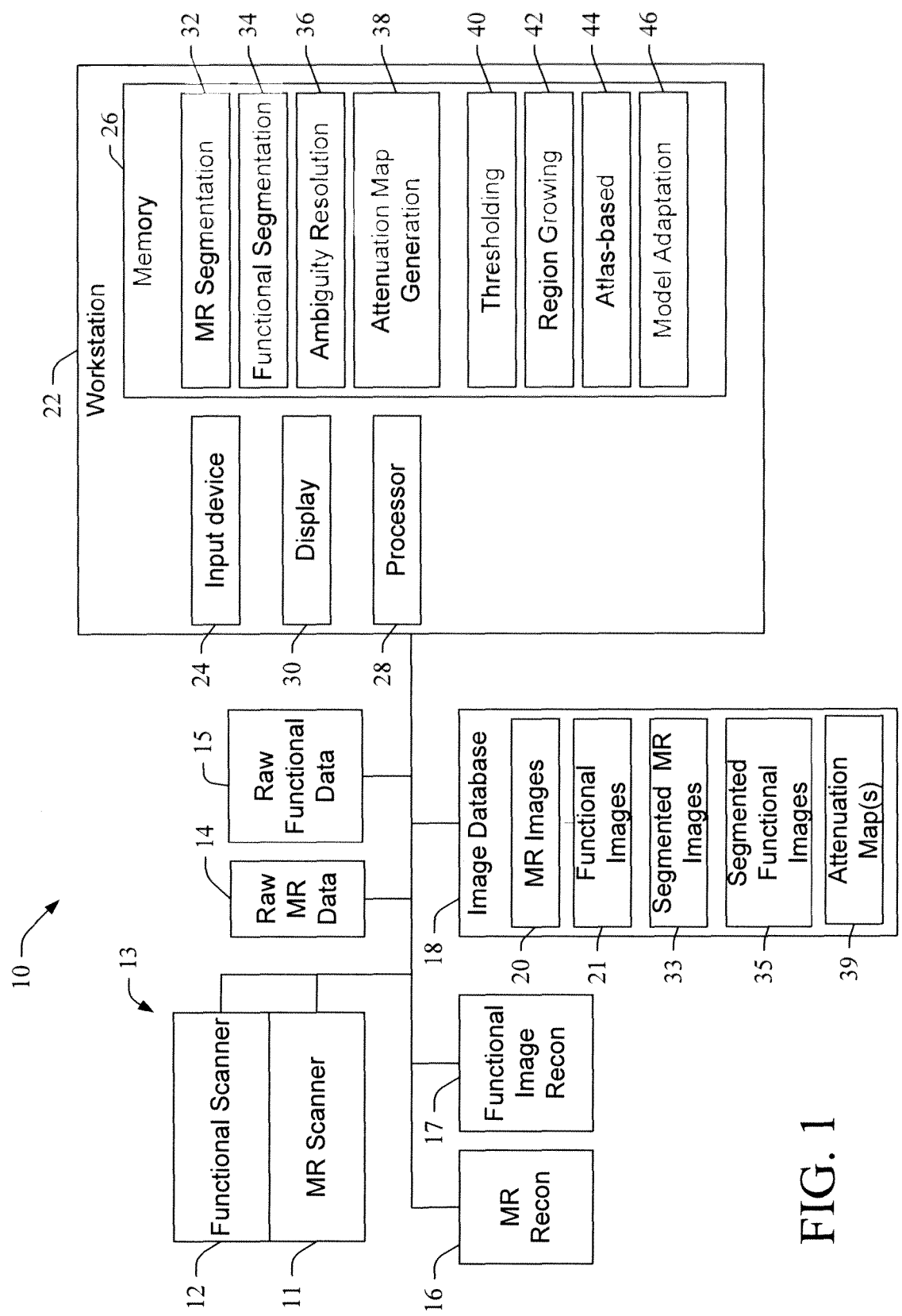
FIG. 1 illustrates a system that facilitates generating an enhanced attenuation map using single or multi-tracer functional (e.g., PET, including variants thereof such as time-of-flight PET (TOF-PET), etc.) imaging, in which an attenuation map is derived from an anatomic imaging modality, particularly MR.

FIG. 1 illustrates a system 10 that facilitates generating an enhanced attenuation map using single or multi-tracer nuclear (e.g., PET, including variants thereof such as time-of-flight PET (TOF-PET), etc.) imaging, in which an attenuation map is derived from an anatomic imaging modality, particularly MR. The system 10 includes an MR scanner 11 and a functional image or nuclear scanner 12. In one embodiment, the MR scanner and nuclear scanner are separate scanners. In another embodiment, the MR scanner 11 and nuclear scanner 12 are housed in a single unit, such as a multi-modal MR/nuclear scanner 13. A subject is scanned using the MR scanner to generate raw MR scan data that is stored in a MR scan data memory or buffer 14. In one embodiment, the MR scan data is acquired before the nuclear scan but after injecting the patient with a radioactive tracer bolus, such as an $^{18}$F radiotracer. The MR scan may be performed before or after the nuclear scan. The subject is also scanned using the nuclear scanner 12 to acquire raw nuclear scan data stored in a nuclear raw data memory or buffer 15. The raw MR data is reconstructed by an MR reconstruction processor 16, and the raw nuclear data is reconstructed by a functional image reconstruction processor 17. Optionally, the functional image reconstruction processor 17 performs scatter correction on the acquired nuclear scan data to enhance a functional image reconstructed therefrom. The system further includes an image database 18 that stores MR images 20 generated by the MR reconstruction processor as well as functional images 21 generated by the nuclear reconstruction processor.

The system 10 includes a workstation 22 that includes an input device 24 (e.g., a keyboard, a mouse, a stylus, a touchscreen, a directional pad, a microphone, or any other suitable input device) via which a user enters information into the system. The workstation also includes a memory 26 that stores, and a processor 28 that executes, computer-executable instructions (e.g., routines, programs, algorithms, software code, etc.) for performing the various functions, methods, procedures, etc., described herein. The system further includes a display 30 on which information is presented to the user. Additionally, "module," as used herein, denotes a set of computer-executable instructions, software code, program, routine, or other computer-executable means for performing the described function, or the like, as will be understood by those of skill in the art. Additionally, or alternatively, one or more of the functions described with regard to the modules herein may be performed manually.

The memory may be a computer-readable medium on which a control program is stored, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The memory stores an MR segmentation module 32 that is executed by the processor to segment an MR image 20 of the patient in order to identify different tissues types, such as soft tissue, cortical bone, air pockets, etc., and generate a one or more segmented MR images 33. The segmentation module 32 can also include one or more additional processors to improve processing speeds. In one embodiment, this segmentation is automated. In another embodiment, the segmentation is performed manually or is semi-automated using the input device 24 and the display 30. However, the segmentation of the MR image may leave unresolved ambiguity when attempting to distinguish between cortical bone and air in the MR image. Therefore, the memory stores a functional image segmentation module 34 that facilitates segmentation of a functional nuclear image 21 of the same subject. The nuclear image segmentation procedure can be fully-automated, semi-automated, or manually preformed using the input device 24 and the display 30.

The functional image segmentation module facilitates generating one or more segmented nuclear emission images 35 in which bone, especially cortical bone, and can be distinguished from the rest of the tissues, including air. An ambiguity resolution module 36 compares the segmented bone regions of the nuclear image to the air/bone regions of the segmented MR image to distinguish between bone and air in the MR image, and assigns appropriate radiation attenuation values, μ, to the corresponding voxels. The bone region of the segmented nuclear image and the bone/air region of the segmented MR image can be compared in various ways. To simplify the comparison, basic attenuation properties of the lungs can be used to identify the lung volume to as belonging to the air category. One way to compare the bone and bone/air ambiguity regions is to overlay the bone region and the bone/air ambiguity regions and look at each pair of corresponding voxels in the two regions. If the voxel is in both the nuclear bone region and in the MR air/bone ambiguity region, it is designated as bone. In another approach, the nuclear bone region and the MR air/bone ambiguity region are subtracted. For example, the nuclear image can be segmented by using the MR air/bone ambiguity region as a mask to eliminate any voxels of the nuclear image that are not ambiguous in the MR image, i.e., a first region of the nuclear image is segmented that corresponds to the air/bone ambiguity region of the MR image. This first region is readily segmented between the air region and a bone region. Subtracting the nuclear image bone region from the MR air/bone ambiguous region leaves only the voxels corresponding to air in the MR image. For instance, cortical bone can be assigned a µ of 1.8 (assuming water having a µ value of 1), and air can be assigned a µ value of 0.0. In this manner, the accuracy of the µ values for tissues identified in the segmented MR image is improved. An attenuation map generation module 38 uses the accuracy-enhanced µ value information to generate one or more nuclear emission data-enhanced MR attenuation maps 39. It will be appreciated that the segmentation of the MR image and/or the PET image can be performed automatically, semi-automatically, or manually.

Once the MR attenuation map is generated, the acquired raw functional image data is reconstructed to generate an attenuation corrected functional image that can be displayed on the display 30. In another embodiment, a combined MR-and-attenuation-corrected functional image is generated and presented to a user on the display.

When segmenting the MR and/or functional nuclear images, one or more of a plurality of techniques may be employed. For instance, the memory 26 stores a thresholding module 40 that is executed by the processor 28 to identify voxels having values greater than (or less than) a predetermined threshold value or within a predetermined window. Additionally or alternatively, the memory stores a region-growing module 42 that is executed by the processor to facilitate image segmentation. Additionally, the memory stores an atlas-based segmentation module 44 that facilitates using an atlas of anatomic image segmentations to segment the MR and/or nuclear images by fitting the model to the current image. In another embodiment, the memory stores a model-based segmentation module 46 that is executed by the processor to facilitate segmentation of the MR and/or nuclear images. It will be appreciated that any of the described segmentation techniques may be performed automatically, semi-automatically, or manually.

In one embodiment, the functional scanner is a PET scanner. As is known in the art, when an electron and positron meet, they annihilate, emitting two 511 keV gamma rays that are oppositely directed in accordance with the principle of conservation of momentum. In PET data acquisition, two substantially simultaneous 511 keV gamma ray detection events are presumed to have originated from the same positron-electron annihilation event, which is therefore located somewhere along the "line of response" (LOR) connecting the two substantially simultaneous 511 keV gamma ray detection events. This line of response is also sometimes called a projection, and the collected PET data is referred to as projection data. In conventional PET, substantially simultaneous 511 keV gamma ray detection events are defined as two 511 keV gamma ray detection events occurring within a selected short time window, such as within one nanosecond of each other. Due to the variable annihilation position with respect to the detector elements a small (e.g., sub-nanosecond) time difference between the substantially simultaneous gamma photon detection events occurs.

In another embodiment, the PET scanner is a time-of-flight (TOF) PET scanner. TOF PET imaging takes advantage of this small time difference to further localize the positron-electron annihilation event along the line-of-response. In general, the annihilation event occurred along the projection at a point closer to the gamma ray detection event that occurred first. If the two gamma ray detection events occur simultaneously within the time resolution of the detectors, then the annihilation event occurred at the midpoint of the projection.

In another embodiment, the functional scanner is a single photon emission computed tomography (SPECT) scanner. In SPECT imaging, one or more radiopharmaceutical or radioisotopes is administered to the imaged subject such that emission radiation is emitted therefrom, as discussed above. Detector heads mounted to a rotating gantry are rotated around the subject to detect radiation from a plurality of directions. The detector heads may rotate around the imaging subject in a 360° revolution taking scans at multiple discrete locations along revolution. Alternatively, the detector heads may rotate over a smaller arc or make multiple revolutions around the subject. The emission projection data or measured sinogram received by the detector heads is reconstructed to generate a SPECT image. Reconstruction techniques employed to reconstruct the emission data may include without limitation iterative reconstruction, Fourier transform-based reconstruction, filtered backprojection, or some other suitable reconstruction technique.

In another embodiment, the nuclear scan data is acquired in list mode. List mode projection data typically includes a list of the detected events, with each entry in the list including information such as a time at which the event was detected, as well as the position and orientation of the corresponding LOR. In the case of a scanner having TOF capabilities, an estimate of the position of the annihilation along the LOR is also provided. Alternately, the acquired data may be sorted or binned into sinogram or projection bins.

The MR scanner is capable of generating detailed images of soft tissues. In MR imaging, specific properties of various compounds found inside tissues are used to generate images, e.g. water is most commonly used for this purpose. When subjected to a strong external magnetic field, the protons align with the external field, resulting in a net magnetic moment. After excitation by radio frequency RF pulses, this magnetization generates a radio frequency (RF) signal that can be detected. The RF signal is characterized by a frequency that is related to the magnetic field strength. Therefore, magnetic field gradients are used to encode spatial information which is used to reconstruct the image from detected signals.

Figure 2:
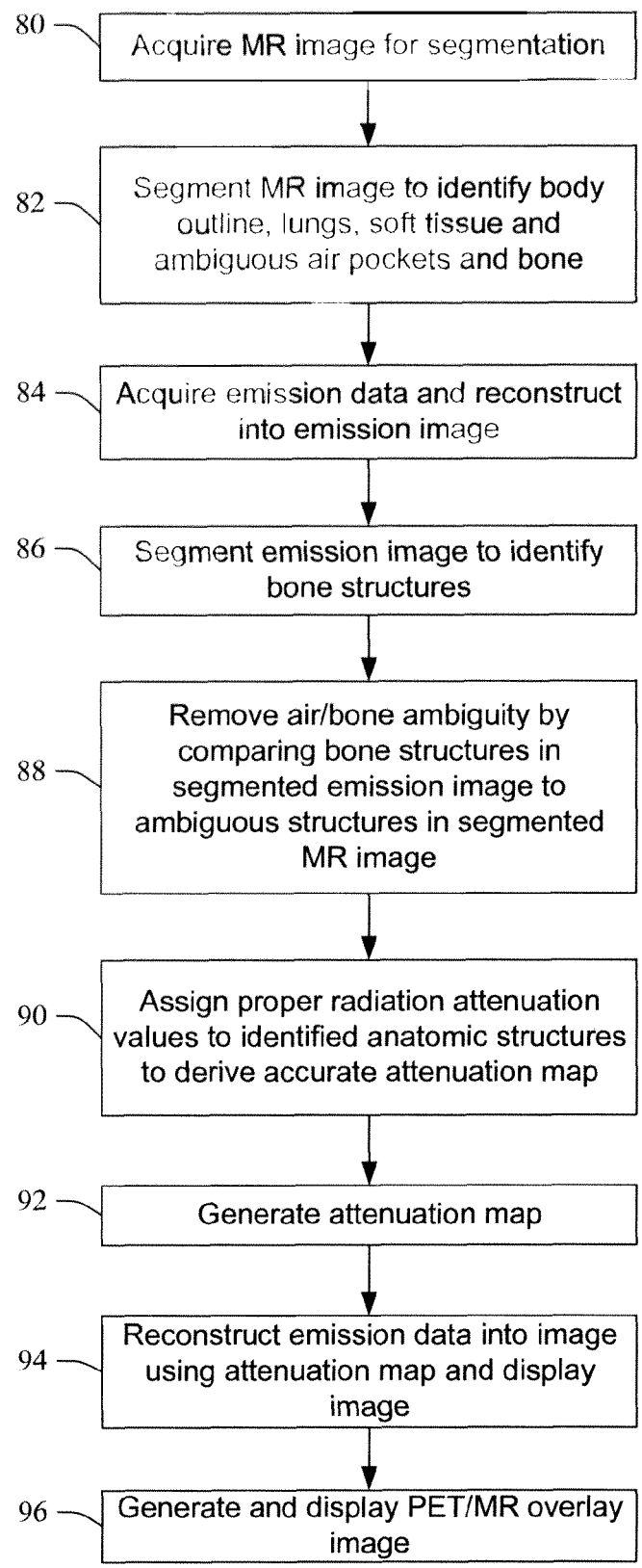
FIG. 2 illustrates a method of generating an enhanced attenuation map using single or multi-tracer functional imaging, in which an attenuation map is derived from an anatomic imaging modality such as MR.

FIG. 2 illustrates a method of generating an enhanced attenuation map using single or multi-tracer nuclear imaging, in which an attenuation map is derived from an anatomic imaging modality, particularly MR. At 80, MR scan data is acquired and reconstructed into an MR image for (a) segmentation, and (b) combining with the PET image to create a combined image that represents both anatomical and functional information about the patient. In one embodiment, the MR scan data is acquired after injecting the patient with a radioactive tracer bolus, such as an $^{18}$F radiotracer or radiopharmaceutical. At 82, the MR image is segmented to identify body outline, lungs, and soft tissues, etc., and air/bone ambiguous regions can be bone or air, such as air pockets in cortical bone structures. At 84, emission data of the same subject is acquired with a single or multi-tracer injected and reconstructed to generate a first-order emission image, i.e., an emission image without attenuation correction. At 86, the first order emission image is segmented to identify bone, particularly cortical bone structures based on an uptake of the $^{18}$F tracer. At 88, ambiguity between air and bone voxels in the MR image is resolved by comparing the voxels of the bone regions identified in the emission image segmentation with the corresponding voxels in the air/bone ambiguous region of the MR image. At 90, radiation attenuation values, µ, are assigned and/or corrected for identified anatomic structures in the segmented MR image to derive an accurate attenuation map. For instance, soft tissue such as fat, muscle, organs, etc., may have an assigned μ value of approximately 1.0, and this value is determined from the segmented MR image. Cortical bone has a μ of approximately 1.8; whereas air has a μ value of approximately 0.0. However, since air and cortical bone cannot be distinguished accurately using the segmented MR image, the segmented emission image is employed to resolve the ambiguity there between, and the cortical bone tissue identified in the emission image is then assigned a μ value of 1.8 in the MR image while the air voxels in the MR image are assigned a value of 0.0. At 92, an enhanced MR attenuation map is generated using the corrected μ values as determined from the segmented emission image. At 94, the raw PET data is reconstructed using the attenuation map and displayed to a user. At 96, a PET/MR overlay image is optionally generated and displayed to the user, the overlay image including the PET image reconstructed using the attenuation map, and the MR image in which bone/air ambiguity has been resolved.

In one embodiment, the MR image segmentation at 82 and/or the PET image segmentation at 86 may use any of a variety of techniques, including but not limited to thresholding, region growing, atlas-based method, model adaptation, or combination of one or more of the above methods with empirical reasoning, etc.

In another embodiment, to derive a better cortical bone structure identification at 86, an emission image is used that is reconstructed from emission data acquired with an injected radioactive tracer which enhances bone structures such as $^{18}F$ sodium fluoride. In another embodiment, a multi-tracer injection is employed. In another embodiment, an inhaled tracer (e.g., Xenon or the like) is used.

In another embodiment, the method is performed iteratively. For instance, multiple nuclear images and/or multiple MR images can be acquired and employed to refine an MR attenuation map, where each successive attenuation map is improved relative to the last and is employed to correct attenuation in one or more of the PET images.

Figure 3:
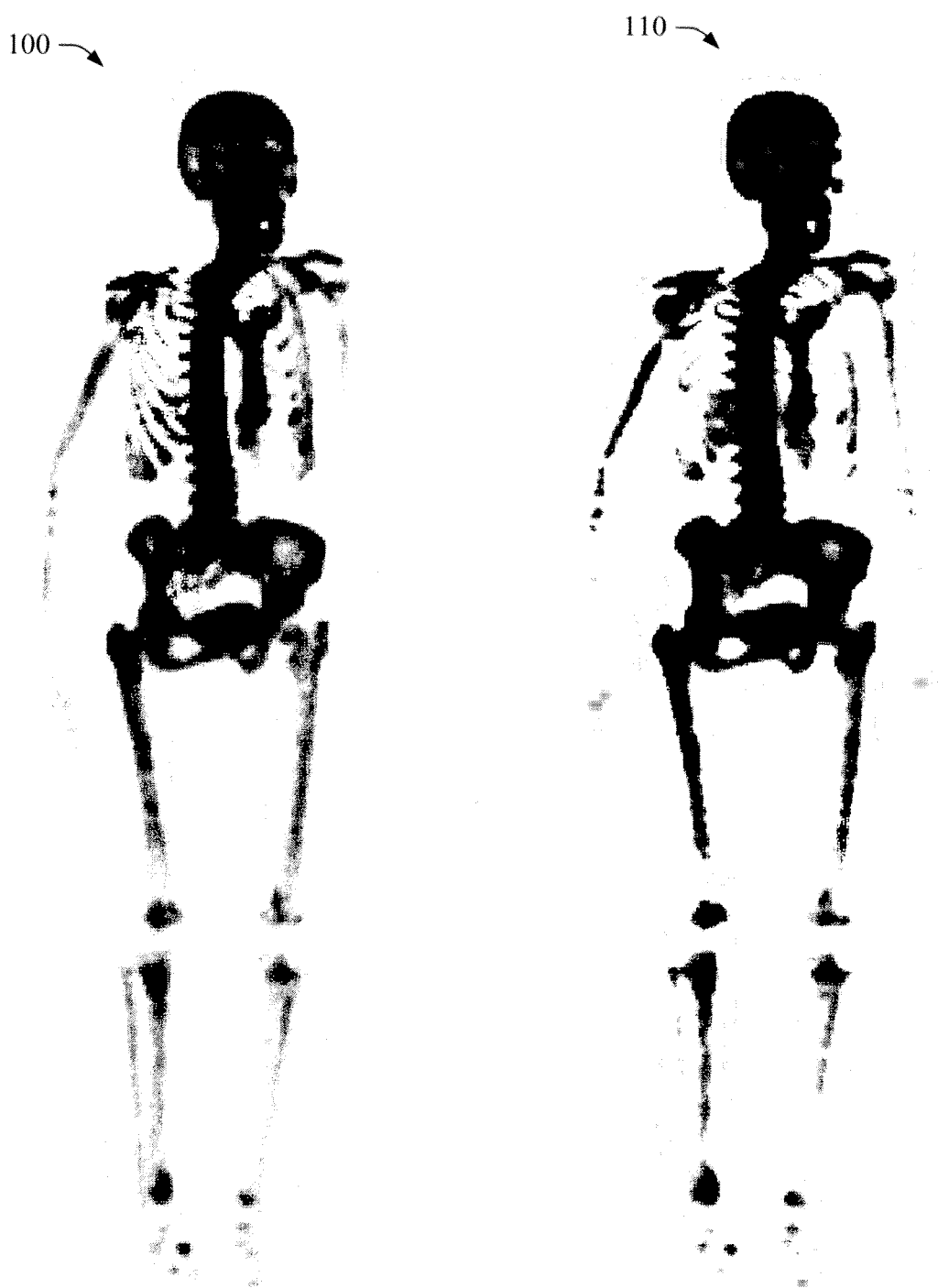
FIG. 3 shows a comparative illustration of an $^{18}$F sodium fluoride PET whole body anatomic image.

FIG. 3 shows a comparative illustration of an $^{18}F$ sodium fluoride PET anatomic image. An original PET image 100 is shown on the left. On the right is an enhanced image 110 showing segmented bone structures that have been identified using a thresholding approach, in accordance with one or more aspects described herein. The segmented PET image 110 can be employed to correctly distinguish between bone and air in a segmented MR image. In one embodiment, the segmented PET image 110 is overlaid on a segmented MR image to align the identified bone voxels in the segmented PET image with ambiguous voxels in the segmented MR image. In this manner, the corresponding ambiguous voxels in the MR image are resolved as bone voxels and assigned appropriate μ values. Remaining ambiguous MR voxels are determined to be air voxels.

It will be appreciated that although the foregoing systems and methods are described with regard to using nuclear emission data to resolve ambiguity between cortical bone and air in an MR image segmentation to enhance MR attenuation map accuracy, they are not limited thereto. Rather, the described systems and methods may be employed to resolve ambiguity between any tissue types, using appropriate radiotracers designed to be absorbed by the ambiguous tissue types.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A system that facilitates resolving ambiguity in a magnetic resonance (MR) image or attenuation map, including:
   an MR reconstruction processor that generates an MR image from raw MR data acquired during a scan of a subject by an MR scanner;
   a functional image reconstruction processor that generates a functional image from functional image data acquired during a scan of a subject by a functional image scanner; and
   a processor programmed to:
      segment the MR image to generate a segmented MR image having a region of air/bone ambiguity in which ambiguity between air voxels and bone voxels is unresolved;
      segment the functional image to generate a segmented functional image having bone regions;
      compare bone regions in the segmented functional image to the bone/air ambiguity region in the segmented MR image to resolve ambiguity between voxels in the bone/air region in the segmented MR image, which correspond to bone and air;
      assign radiation attenuation values consistent with bone to identified bone voxels, and consistent with air to identified air voxels, in the segmented MR image; and
      generate an MR attenuation map using the assigned radiation attenuation values.

2. The system according to claim 1, wherein the functional image data includes emission data from a PET scanner and is acquired using a single radiotracer.

3. The system according to claim 2, wherein the radiotracer includes an 18F isotope of fluoride.

4. The system according to claim 1, wherein the processor is programmed to:
   overlay at least one bone region of the segmented functional image and at least one anatomically corresponding air/bone ambiguity region in the segmented MR image;
   identify pairs of corresponding voxels in the bone region and in the air/bone ambiguity region; and
   identify voxels in the air/bone ambiguity region of the segmented MR image that have a corresponding voxel in the bone region of the segmented functional image as bone voxels in the segmented MR image.

5. The system according to claim 1, wherein the processor is programmed to:
   overlay at least one air region of the segmented functional image and at least one anatomically corresponding air/bone ambiguity region in the segmented MR image;
   identify pairs of corresponding voxels in the air region and in the air/bone ambiguity region;
   subtract the air region from the air/bone ambiguity region; and
   identify remaining voxels in the air/bone ambiguity region as bone voxels.

6. The system according to claim 1, wherein the functional image scanner is at least one of:
   a positron emission tomography (PET) scanner that acquires the functional image data; and
   a single photon emission computed tomography (SPECT) scanner that acquires the functional image data.

7. The system according to claim 6, wherein the PET scanner and the MR scanner are included in a single multimodal PET/MR scanning device.

8. The system according to claim 1, wherein the processor is further programmed to:
execute a thresholding module to segment at least one of the MR image and the functional image.

9. The system according to claim 1, wherein the processor is further programmed to:
execute a region growing module to segment at least one of the MR image and the functional image.

10. The system according to claim 1, wherein the processor is further programmed to:
execute an atlas-based segmentation module to segment at least one of the MR image and the functional image.

11. The system according to claim 1, wherein the processor is further programmed to:
execute a model-based adaptation module to segment at least one of the MR image and the functional image.

12. A method of resolving ambiguity in a magnetic resonance (MR) image or attenuation map, including:
generating an MR image from raw MR data acquired during a scan of a subject by an MR scanner;
generating a functional image from functional image data acquired during a scan of a subject by a functional image scanner;
segmenting the MR image to generate a segmented MR image having a region of air/bone ambiguity in which ambiguity between air voxels and bone voxels is unresolved;
segmenting the functional image to generate a segmented functional image having bone regions and other tissue regions;
comparing the bone regions in the segmented functional image to the bone/air ambiguity region in the segmented MR image to resolve ambiguity between voxels in the bone/air region in the segmented MR image, which correspond to bone and air;
assigning radiation attenuation values consistent with bone to identified bone voxels, and consistent with air to identified air voxels, in the segmented MR image;
generating an MR attenuation map using the assigned radiation attenuation values;
reconstructing the functional image data into an image using the MR attenuation map to correct attenuation in the functional image data; and
displaying the image on a display to a user.

13. The method according to claim 12, wherein the functional image data includes emission data from a PET scanner and is acquired using a single radiotracer.

14. The method according to claim 13, wherein the radiotracer includes an 18F isotope of fluoride.

15. The method according to claim 12, further including:
overlaying at least one bone region of the segmented functional image and at least one anatomically corresponding air/bone ambiguity region in the segmented MR image;
identifying pairs of corresponding voxels in the bone region and in the air/bone ambiguity region; and
identifying voxels in the air/bone ambiguity region of the segmented MR image that have a corresponding voxel in the bone region of the segmented functional image as bone voxels in the segmented MR image.

16. The method according to claim 12, further including:
overlaying at least one air region of the segmented functional image and at least one anatomically corresponding air/bone ambiguity region in the segmented MR image;
identifying pairs of corresponding voxels in the air region and in the air/bone ambiguity region;
subtracting the air region from the air/bone ambiguity region; and
identifying remaining voxels in the air/bone ambiguity region as bone voxels.

17. The method according to claim 12, wherein the functional scanner is at least one of:
a positron emission tomography (PET) scanner that acquires the functional image data; and
a single photon emission computed tomography (SPECT) scanner that acquires the functional image data.

18. The method according to claim 17, wherein the PET scanner and the MR scanner are included in a single multimodal PET/MR scanning device.

19. The method according to claim 12, wherein segmenting at least one of the MR image and the functional image is performed using at least one of:
a thresholding technique;
a region growing technique;
an atlas-based segmentation technique; and
a model-based adaptation technique.

20. A processor or computer-readable medium carrying a computer program that controls one or more processors to perform the method of claim 12.

21. A system for generating functional images, comprising:
a processor programmed to perform the method according to claim 12 to generate an attenuation map;
a reconstruction processor programmed to reconstruct the functional image data using the attenuation map to generate and attenuation-corrected functional image; and
a display that displays at least one of the attenuation-corrected functional image and a combined MR-and-attenuation-corrected functional image.

22. A method of enhancing a magnetic resonance (MR) attenuation map using nuclear emission data, including:
segmenting, with at least one processor, an MR image to identify soft tissue structures and ambiguous structures in the MR image, the ambiguous structures including one or more of bone and air;
segmenting, with the at least one processor, a nuclear image to identify bone structures in the nuclear image;
overlaying, with the at least one processor, the segmented nuclear image on the segmented MR image;
identifying, with the at least one processor, the ambiguous structures in the segmented MR image as either bone or air by comparing the ambiguous structures to the bone structures in the overlaid segmented nuclear image;
assigning, with the at least one processor, a first radiation attenuation value to bone voxels identified in the segmented MR image, and a second radiation attenuation value to air voxels in the segmented MR image; and
generating, with the at least one processor, an MR attenuation map from the segmented MR image.

* * * * *